(12) United States Patent
Carpenter

(10) Patent No.: US 12,396,883 B2
(45) Date of Patent: *Aug. 26, 2025

(54) SYSTEM FOR GENERATING AND APPLYING HEATED AIR TO THE HUMAN BODY

(71) Applicant: Joseph Carpenter, Las Vegas, NV (US)

(72) Inventor: Joseph Carpenter, Las Vegas, NV (US)

( * ) Notice: Subject to any disclaimer, the term of this patent is extended or adjusted under 35 U.S.C. 154(b) by 257 days.

This patent is subject to a terminal disclaimer.

(21) Appl. No.: 18/075,290

(22) Filed: Dec. 5, 2022

(65) Prior Publication Data
US 2023/0099365 A1  Mar. 30, 2023

Related U.S. Application Data

(63) Continuation-in-part of application No. 16/427,937, filed on May 31, 2019, now Pat. No. 11,540,938.

(51) Int. Cl.
*A61F 7/00* (2006.01)

(52) U.S. Cl.
CPC .... *A61F 7/0085* (2013.01); *A61F 2007/0048* (2013.01); *A61F 2007/006* (2013.01); *A61F 2007/0091* (2013.01)

(58) Field of Classification Search
CPC .......... A61F 7/0085; A61F 7/086; A61F 2007/0057; A61F 2007/083; A61F 2007/0091
See application file for complete search history.

(56) References Cited

U.S. PATENT DOCUMENTS 11,540,938 B2 * 1/2023 Carpenter ............. A61F 7/0085

* cited by examiner

*Primary Examiner* — Kaitlyn E Smith
(74) *Attorney, Agent, or Firm* — The Thornton Firm, LLC

(57) ABSTRACT

Disclosed is a system and method for producing and storing hot air, and for applying the stored hot air to a human body. The hot air producing system may include a heating apparatus configured to heat air to a temperature, a temperature setting gauge, a pressure gauge, a pump to pump the hot air, a fill connection, a container for receiving hot air from the heating apparatus and storing the hot air therein, the container including at least one valve to connect to the fill connection of the heating apparatus such that the container can receive the hot air from the heating apparatus, an adjustable flow release mechanism connected to an outlet of the container for receiving the hot air, and a flexible hose connected to the adjustable flow release mechanism. Embodiments of the invention can include a computer system capable of governing all the components.

19 Claims, 8 Drawing Sheets

SYSTEM FOR GENERATING AND APPLYING HEATED AIR TO THE HUMAN BODY

CROSS-REFERENCE TO RELATED APPLICATIONS

The present continuation-in-part application claims priority benefit of the U.S. nonprovisional application for patent Ser. No. 16/427,937 titled "Medical Hot Air Blower" filed on May 31, 2019 under 35 U.S.C. § 119(e). The contents of this related nonprovisional application are incorporated herein by reference for all purposes to the extent that such subject matter is not inconsistent herewith or limiting hereof.

RELATED CO-PENDING U.S. PATENT APPLICATIONS

Continuation-in-part application of U.S. nonprovisional application for patent Ser. No. 16/427,937 titled "Medical Hot Air Blower" filed on May 31, 2019 under 35 U.S.C. § 119(e).

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

BACKGROUND OF THE INVENTION

1. Field of the Invention

The invention relates generally to medical devices. More specifically, the invention relates to a system for generating and applying heated air to the human body to treat medical conditions.

2. Description of the Related Art

Urinary retention is a condition where a human can't pass urine even though the person may have a full bladder. This condition can have many causes, such as certain infections or medication, weakened bladder muscles, an injury to the pelvic or genital regions, any surgery requiring sedation or recent surgery in the genital, prostrate, rectal, pelvic or lower abdominal areas. There are also times when passing urine is required, however a person may not be able to void on command, such as for medical samples or after sexual intercourse to test for or avoid urinary tract infections. A known method of treatment of this condition is to apply heat to the genital area using water or a warm compress. However, applying heat using a heated air device is not common practice and while using such a device it is essential to produce heated air of the correct temperature which can be difficult. While certain conventional heated air devices could be used in non-conventional ways, these devices often produce unregulated heated air in excess of 140 degrees Fahrenheit, which could easily cause burns or discomfort to this very sensitive area of the human body.

Accordingly, a new apparatus is needed to apply heated air to this sensitive genital area of the human body.

SUMMARY

The present invention is directed to an improved system for generating and applying heated air to the human body to treat medical conditions. Such a system and method overcomes the limitations which currently exist in traditional systems.

The present invention is directed to an improved system for generating and applying heated air to the human body which includes a hot air producing system for producing and storing hot air, and for applying the stored hot air to a human body. The hot air producing system may include a heating apparatus configured to heat the air to a temperature, the heating apparatus including a temperature setting gauge configured to allow a user to set a desired temperature to heat the air, a pressure gauge to measure a pressure of the air in the container, a pump to pump the hot air, and a fill connection; an expandable container for receiving the hot air from the heating apparatus and storing the hot air therein, the expandable container including a valve to connect to the fill connection of the heating apparatus such that the expandable container can receive the hot air from the heating apparatus; an adjustable flow release mechanism connected to an outlet of the expandable container, the adjustable flow release mechanism being configured to allow a user to adjust an amount of flow of hot air out of the expandable container; and a flexible hose connected to the adjustable flow release mechanism, the flexible hose having a nozzle configured to direct the hot air out of the flexible hose, wherein the flexible hose allows a user to direct the hot air to a portion of the human body.

The hot air producing system may further include an insulated case for receiving the container therein, the insulated case comprising a material having insulative properties to retain heat in the hot air in the container.

Additional embodiments of the invention can include a heating apparatus configured to heat air to a temperature, the heating apparatus including a temperature setting gauge configured to allow a user to set a desired temperature to heat the air, a pressure gauge to measure a pressure of the air, a pump to pump the hot air, a fill connection, a container for receiving hot air from the heating apparatus and storing the hot air therein, the container including at least one valve to connect to the fill connection of the heating apparatus such that the container can receive the hot air from the heating apparatus, an adjustable flow release mechanism connected to an outlet of the container for receiving the hot air, the adjustable flow release mechanism being configured to allow a user to adjust an amount of flow of hot air out of the said container, a flexible hose connected to the adjustable flow release mechanism, the flexible hose having a nozzle configured to direct the hot air out of the flexible hose, wherein the flexible hose allows a user to direct the hot air to a portion of the human body. Such an embodiment allows for the use of a rigid container for receiving hot air from the heating apparatus as opposed to a flexible container.

An alternative embodiment of the invention includes a heating apparatus configured to heat air to a temperature, the heating apparatus including a temperature setting gauge configured to allow a user to set a desired temperature to heat the air, a pressure gauge to measure a pressure of the air, a heating apparatus configured to heat air to a desired temperature, an air blower for moving air from an air inlet through the system for producing and storing hot air, and for applying the stored hot air to a human body, a fill connection, a container for receiving hot air from the heating apparatus and storing the hot air therein, the container including at least one valve to connect to the fill connection of the heating apparatus such that the container can receive the hot air from the heating apparatus, an adjustable flow release mechanism connected to an outlet of the container for receiving the hot air, the adjustable flow release mechanism being configured to allow a user to adjust an amount of flow of hot air out of the said container, a flexible hose connected to the adjustable flow release mechanism, the flexible hose having a nozzle configured to direct the hot air out of the flexible hose, wherein the flexible hose allows a user to direct the hot air to a portion of the human body, a controller unit including at least one processor, and a display. Such an embodiment can be configured to function as an integrated unit capable of being used in a larger setting such as, but not limited to, hospitals and managed care settings.

Another embodiment of the invention includes an air inlet, an air chamber for receiving air, a filtering and sanitizing mechanism for filtering and sanitizing air entering the hot air producing and storing apparatus, an air blower for moving air from the air inlet through the hot air and storing apparatus, a heating apparatus configured to heat air to a temperature, the heating apparatus including a temperature setting gauge configured to allow a user to set a desired temperature to heat the air, a pressure gauge to measure a pressure of the air, a pump to pump the hot air, and a fill connection, a hot air chamber for receiving the hot air from the heating apparatus and storing the hot air therein, the hot air chamber including a valve to connect to the fill connection of the heating apparatus such that the hot air chamber can receive the hot air from the heating apparatus, an insulated case for receiving the hot air chamber therein, the insulated case comprising a material having insulative properties to retain heat in the hot air chamber, and a flexible hose connected to the adjustable flow release mechanism, the flexible hose having a nozzle configured to direct the hot air out of the flexible hose, wherein the flexible hose allows a user to direct the hot air to a portion of the human body, a controller unit including at least one processor, and a display. Such an embodiment employs updated technology and is capable of networking with other suitable devices to provide a safer and improved system.

The invention also includes a controller unit for governing functions of the multiple components of the invention. The controller unit includes at least one processor and memory to cause the system to perform the functions of powering up the system, powering up a heating apparatus configured to heat air to a desired temperature, setting the temperature of the air stored in the container for receiving hot air from the heating apparatus, engaging the air blower adjusting the flow release mechanism connected to an outlet of the container for receiving hot air from the heating apparatus, adjusting the air pressure in the container for receiving hot air from the heating apparatus, adjusting the air flow rate for the air emerging from the system, and powering down the system when the heating cycle is complete.

Alternative embodiments of the invention can include a filtering and sanitizing mechanism for providing filtered and sanitized heated air to be applied to a human body. Other embodiments include a self-contained unit which can be easily moved from room to room.

BRIEF DESCRIPTION OF THE DRAWINGS

The invention directed by way of example, and not by way of limitation, in the figures of the accompanying drawings and in which like reference numerals refer to similar elements and in which.

Figure 1:
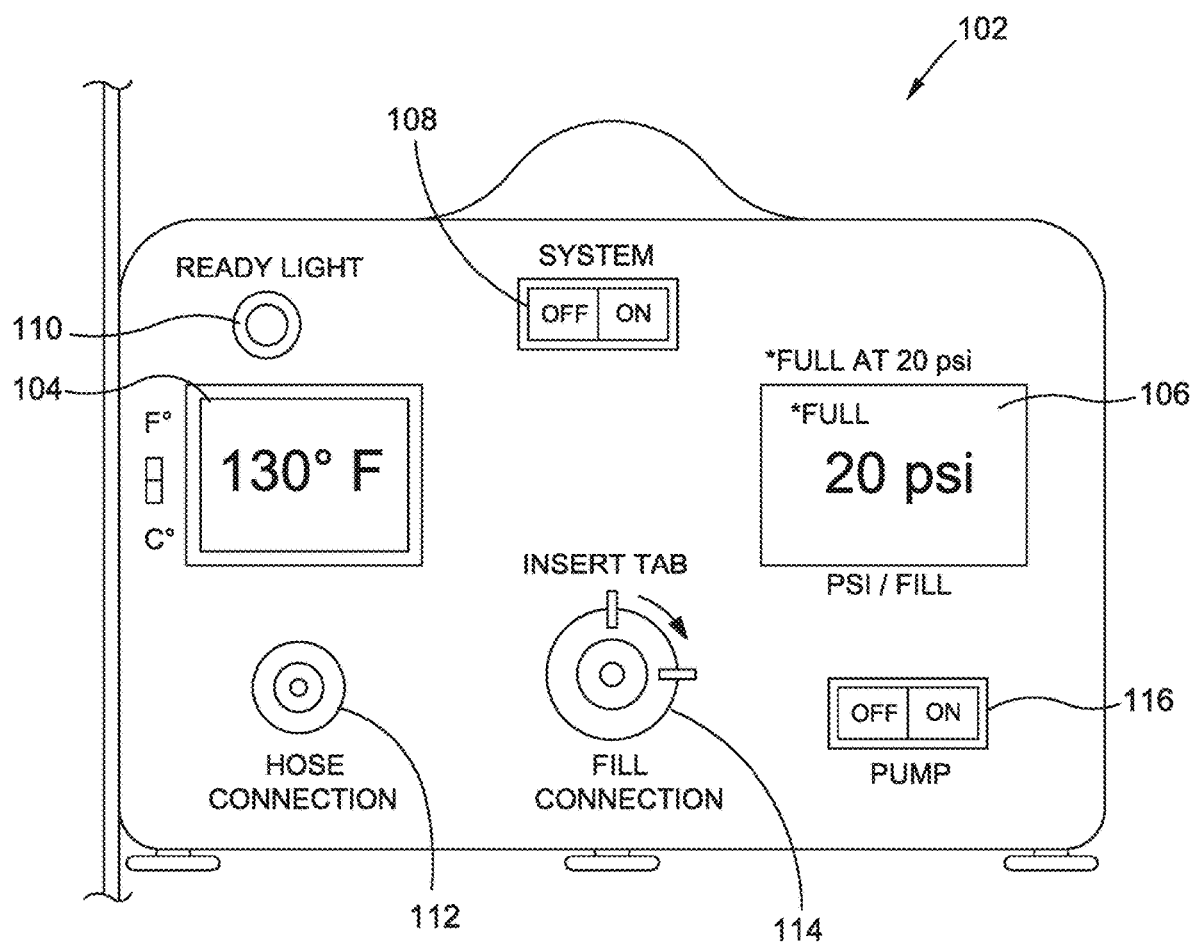
FIG. 1 is a front perspective view of a system for generating and applying heated air to the human body in accordance with an embodiment of the invention.

Unless otherwise indicated illustrations in the figures are not necessarily drawn to scale.

DETAILED DESCRIPTION OF THE PREFERRED EMBODIMENTS

Terminology used herein is used for the purpose of describing particular embodiments only, and is not intended to limit the scope of the present invention. It must be understood that as used herein and in the appended claims, the singular forms "a," "an," and "the" include the plural reference unless the context clearly dictates otherwise. For example, a reference to "an element" is a reference to one or more elements and includes all equivalents known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Language that may be construed to express approximation should be so understood unless the context clearly dictates otherwise.

Unless defined otherwise, all technical and scientific terms used herein have the same meanings as commonly understood by a person of ordinary skill in the art to which this invention belongs. Preferred methods, techniques, devices, and materials are described. But any methods, techniques, devices, or materials similar or equivalent to those described herein may be used in the practice or testing of the present invention. Structures described herein should also be understood to refer to functional equivalents of such structures.

References to "one embodiment," "one variant," "an embodiment," "a variant," "various embodiments," "numerous variants," etc., may indicate that the embodiment(s) of the invention so described may include particular features, structures, or characteristics. However, not every embodiment or variant necessarily includes the particular features, structures, or characteristics. Further, repeated use of the phrase "in one embodiment," or "in an exemplary embodiment," or "a variant," or "another variant," do not necessarily refer to the same embodiment although they may. A description of an embodiment with several components in communication with each other does not imply that all such components are required. On the contrary, a variety of optional components are described to illustrate the wide variety of possible embodiments and/or variants of the present invention.

A "computer" may refer to one or more apparatus and/or one or more systems that are capable of accepting a structured input, processing the structured input according to prescribed rules, and producing results of the processing as output. Examples of a computer may include: a personal computer (PC); a stationary and/or portable computer; a computer having a single processor, a computer having multiple processors, or a computer having multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer; a personal digital assistant (PDA); a portable telephone; a portable smartphone; wearable devices such as smartwatches; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

The term "processor" may refer to any device or portion of a device that processes electronic data from registers and/or memory to transform that electronic data into other electronic data that may be stored in registers and/or memory. A "computing platform" may comprise one or more processors.

A "microcontroller" generally refers a small computer on a single integrated circuit. A microcontroller contains one or more central processing units (processor cores) along with memory and programmable input/output peripherals. A typical microcontroller includes a processor, memory and input/output (I/O) peripherals on a single chip.

An "algorithm" is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

It will be readily understood by persons skilled in the art that the various methods and algorithms described herein may be implemented by appropriately programmed computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

"Software" may refer to prescribed rules and/or instructions used to operate a computer. Examples of software may include: code segments in one or more computer-readable languages; graphical and or/textual instructions; applets; pre-compiled code; interpreted code; compiled code; and computer programs. An operating system or "OS" is software that manages computer hardware and software resources and provides common services for computer programs.

Certain embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages or other compilers, assemblers, interpreters or other computer languages or platforms.

A "computer system" may refer to a system having one or more computers, where each computer may include a computer-readable medium employing software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a plurality of computers and associated devices that may be connected by communication channels to facilitate communication and resource sharing.

A network may involve permanent connections such as cables or temporary connections such as those made through telephone, cable, wireless or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include, but are not limited to, an internet, such as the Internet or World Wide Web; an intranet; a personal area network (PAN); near field communication (NFC); a local area network (LAN); a wide area network (WAN); a virtual private network (VPN); internet of things (IoT); and a combination of networks, such as an internet and an intranet.

Aspects of the exemplary system for generating and applying heated air to the human body to treat medical conditions will be described below with reference to flowchart illustrations and/or block diagrams of methods, steps, apparatus (systems) and computer program products according to embodiments of the invention. Persons skilled in the art will understand that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, microcontroller, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods, and computer program products according to various embodiments of the exemplary system for generating and applying heated air to the human body to treat medical conditions. It will become readily apparent to persons skilled in the art that each block in the flowchart or block diagrams may represent a module, segment, or portion of code, which comprises one or more executable instructions for implementing the specified logical function(s). It will also be readily apparent to persons skilled in the art that in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. Although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any practical order.

It will also be understood by persons skilled in the art that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

It will be readily understood by persons skilled in the art that the various methods and algorithms described herein may be implemented by appropriately programmed computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

As is well known to those skilled in the art, many careful considerations and compromises typically must be made when designing the optimal manufacture or commercial implementation of such a system for generating and applying heated air to the human body to treat medical conditions. A commercial implementation in accordance with the spirit and teachings of the invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art.

The exemplary system for generating and applying heated air to the human body to treat medical conditions now be described in detail with reference to embodiments thereof as illustrated in the accompanying drawings. Unless otherwise indicated illustrations in the figures are not necessarily drawn to scale.

Embodiments of the invention provide a hot air producing apparatus configured to pump the hot air into a container under pressure. The container can then be used to temporarily store the hot or heated air and to apply the hot or heated air to the human body or for other purposes.

A front view of the system for generating and applying heated air to the human body to treat medical conditions 102 is illustrated in FIG. 1 in accordance with preferred embodiments of the invention. The hot air producing apparatus 102 includes an air temperature gauge 104 (which can be switched between Celsius and Fahrenheit), a pressure setting gauge 106, a system power on/off switch 108, a ready light 110, a hose connection 112, a fill connection 114, and a pump on/off switch 116.

The system for generating and applying heated air to the human body to treat medical conditions 102 may include a heater device such as a conventional heat pump to heat air and to pump the heated air under pressure. The heated air may be pumped either through the hose connection 112 or the fill connection 114 to fill a container with the hot air.

The temperature of the hot air can be set using the temperature gauge 104, which can be set to read either Celsius or Fahrenheit. A control (as described below) can be used to adjust the temperature to a desired level, such as with a numeric keypad or touchscreen, or even from a remote source connected to the hot air producing apparatus 102. The pressure gauge 106 can be used to monitor pressure in psi, for example. The hot air producing apparatus 102 can be configured to pump hot air into a container to fill the container to a desired pressure. The hot air producing apparatus 102 can be configured to automatically shut off the pumping of the hot air when the container reaches the desired or a preset pressure.

The system power on/off switch 108 can be used to turn on or off all power to the system. The power may be supplied through a convention power cord, or be supplied by one or more batteries within the hot air producing apparatus 102. The hot air producing apparatus 102 may be configured to have containers receive hot air at any desired temperature and until full. In preferred embodiments, the hot air producing apparatus 102 may fill containers until a full pressure is reached, and the full pressure may be 20 psi as shown in FIG. 1, although other pressures could be used. The hot air producing apparatus 102 may be configured to automatically stop pumping hot air when the full pressure is reached.

The ready light 110 can be used to indicate when the hot air producing apparatus 102 is ready to begin pumping air at the desired temperature. The hot air producing apparatus 102 may need time to warm up a heating element to produce hot air of the desired temperature, and the ready light can thus be used to indicate when the apparatus is sufficiently warmed up to begin pumping the heated air. The hose connection 112 may include a connector adapted to fit a hose with a corresponding connector of a particular type. The type of connectors used can be varied.

The fill connection 114 may be adapted to connect directly to a connector of a container, where a hose is not used. The fill connection 114 may have a connector of a different type than the hose connection 112.

The pump on/off switch 116 is used to turn the pump on (or off) to begin (or stop) pumping hot air through either the hose connection 112 or the fill connection 114. The switch may be configured to not function until the ready light is lit indicating the air can be pumped at the desired temperature.

The hot air producing apparatus 102 may include a processor and a memory (as detailed below), with the memory containing software configured to be run by the processor to control the hot air producing apparatus 102 to perform any of the functionality described herein.

Figure 2:
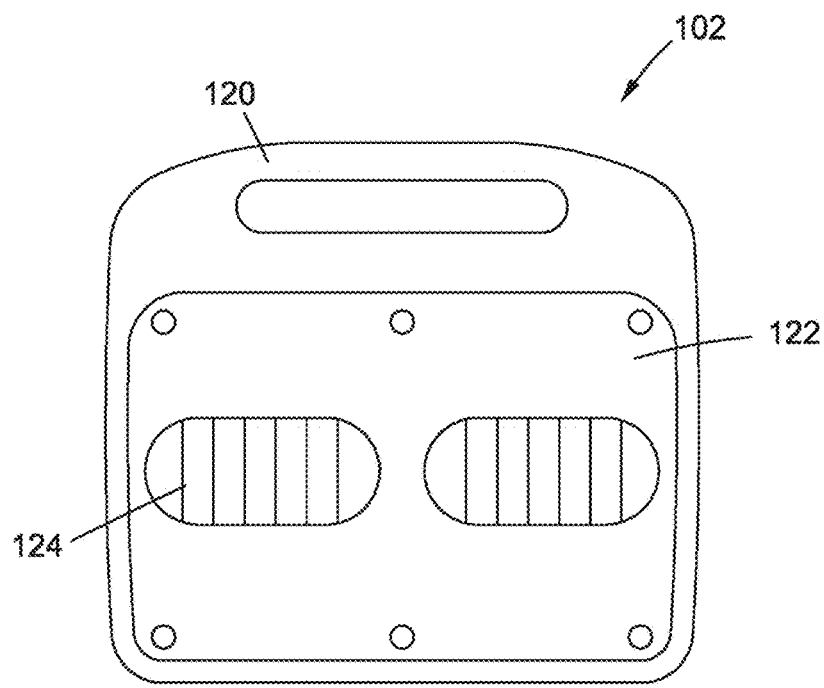
FIG. 2 is a side perspective view of a system for generating and applying heated air to the human body in accordance with an embodiment of the invention.

FIG. 2 illustrates a side view of the hot air producing apparatus 102. The side of the hot air producing apparatus 102 includes a handle 120 for carrying the hot air producing apparatus 102, and air vents 124 to cool the hot air producing apparatus 102. The air vents may be on an access panel 122.

Figure 3:
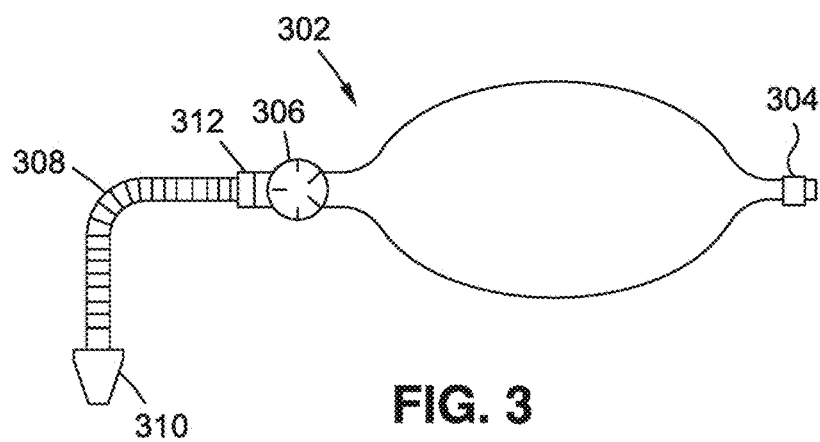
FIG. 3 is a perspective view of a an expandable container for containing heated air in accordance with an embodiment of the invention.

FIG. 3 illustrates a flexible container for containing hot air produced by the hot air producing apparatus 302. The container 302 is configured to function with the hot air producing apparatus, and may be included as a part thereof. The container 302 may include a fill valve 304, an adjustable flow release valve 306, a flexible plastic tube 308, and air nozzle 310 and a connector 312. The container 302 is expandable, and may be an elastic fill bag, for example. The container may be formed from an elastic material such as natural rubber, synthetic rubber, nitrile rubber, silicone rubber, urethane rubber, chloroprene rubber, polyether rubber, chloroprene rubber, Ethylene Vinyl Acetate.

In an alternative embodiment of the invention, the container can be made from a rigid material such as, but not limited to, steel, aluminum, or a rigid plastic capable of storing heated air under pressure.

The fill valve 304 may be configured to connect to the fill connection 114 on the front of the hot air producing apparatus 102. When the pump of the hot air producing apparatus 102 is turned on with the fill valve 304 connected to the fill connection 114, hot air is pumped into the container 302 where the hot air can be stored and later used for application to the human body.

The flow release valve 306 is configured to allow a user to adjust a flow amount of hot air being release by, for example, turning of the valve 306. The flow release valve may include an off position, at which no air is released, and it may allow progressively more air to be release as the valve 306 is turned away from the off position. The connector 312 is adapted to connect the air holding portion of the container 302 to the flexible hose 308. The flow release valve may be positioned on either side of the connector 312, although in a preferred embodiment, the flow release valve is positioned between the connector 312 and the flexible tube 308.

The flexible tube 308 allows the air nozzle 310 to be positioned by a user as desired to direct the hot air to a desired location. The flexible tube 308 may be made from various flexible materials, such as rubber, plastic, polyurethane, PVC, Nomex, Hypalon, thermoplastic, etc.

Figure 4:
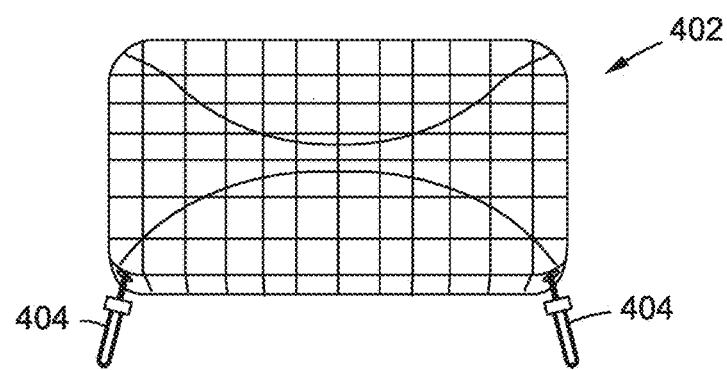
FIG. 4 is a perspective view of an expandable insulated case for retaining an expandable container in accordance with an embodiment of the invention.

FIG. 4 illustrates an insulated case 402 for holding the container 302. The case 402 is insulated to help the air in the container 302 to retain its heated condition over the course of time after the air is put in the container and before it is used. The insulated case may also be formed from a material that is stretchable, so that the case 402 can expand as air is put in the container 302.

For example, the insulated case may be made from materials such as a quilted material, Thinsulate®, or other thermal fabric product to provide insulation, or a stretchable thermo fabric to provide insulation and be stretchable. The case 402 may include one or tightening cords 404 to tighten the case 402 around the container 302. The case 402 may be sized to somewhat tightly fit the container 302 therein, while being able to stretch to a larger size as needed. The case 402 may include one or more zippers (not shown) or other ways of closing the insulated case 402 around the container 302.

Figure 5:
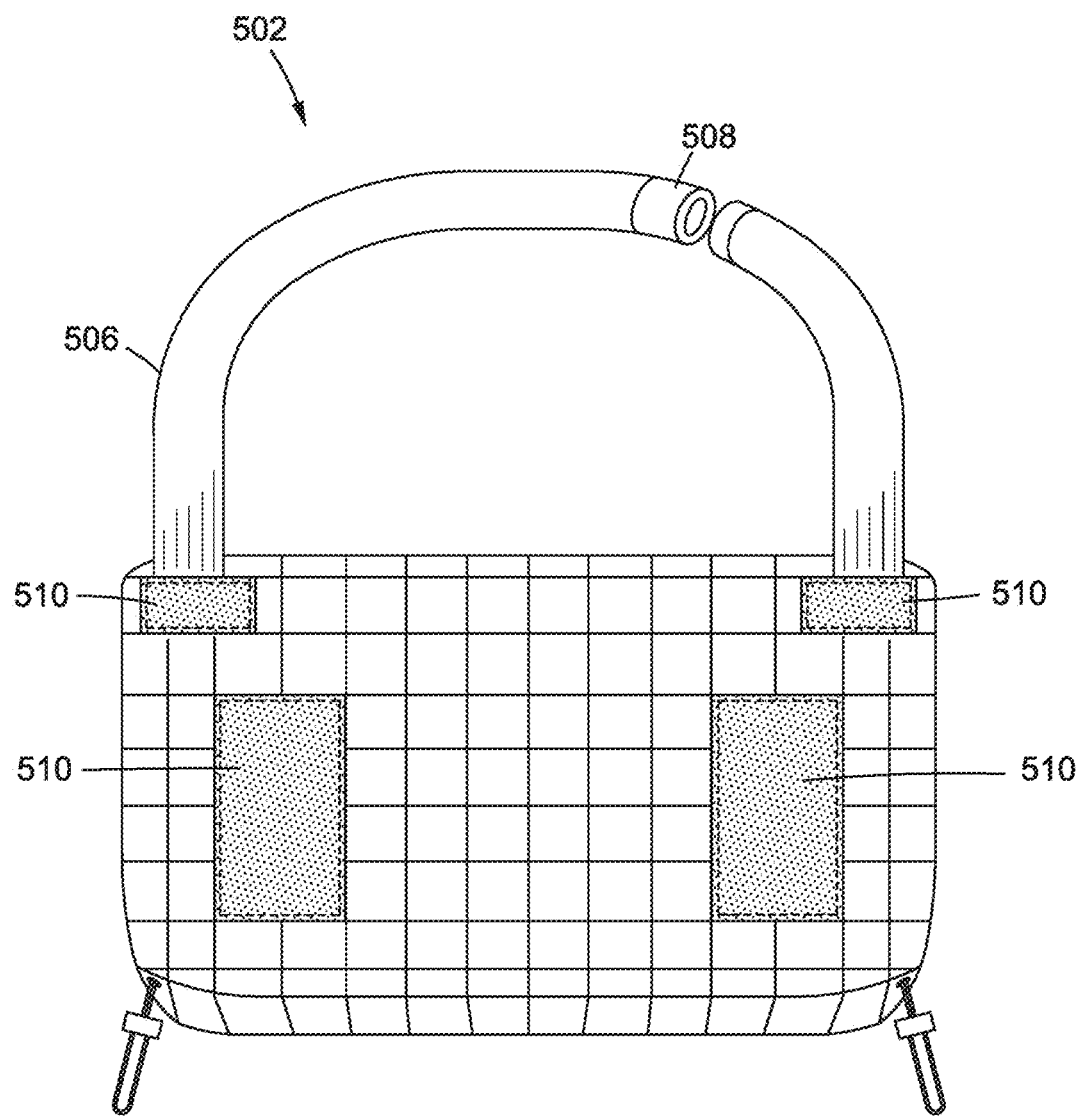
FIG. 5 is a view of an alternate expandable insulated case for retaining an expandable container in accordance with an embodiment of the invention.

FIG. 5 illustrates another insulated case 502 having additional features. The insulated case 502 has a strap or handle 506. The strap 506 may have an adjustable length. The strap 506 may include connectors 508 allowing the strap to be disconnected into two pieces and reconnected. This allows the strap to be connected around objects to retain the insulated case in place. For example, the strap 506 be connected to a hook on a wall or table, to a bed post or rail, to a rail on a bathtub or toilet, around a human wrist, etc.

The insulated case 502 may also include attachment points 510. The attachment points 510 could be Velcro® strips or other means of attachment. The attachment points 510 may be placed at various points on the insulated case 502. Any number of attachment points 510 may be used. Corresponding attachments points may be placed on an object, such as a wall, a bed, a toilet, etc., to which the insulated case 502 is to be attached. For example, if the attachments points 510 are Velcro® strips, corresponding Velcro® strips can be placed on an object to which the insulated case 502 is to be attached.

The system for generating and applying heated air to the human body may be implemented as a hand-held device, or as a movable unit which may be rolled from room to room. The system for generating and applying heated air to the human body may be configured to function in environments ranging from hospital care to home care. Persons skilled in the art will readily appreciate that numerous means are available for implementing and performing the function of applying heated air to sensitive areas of the human body.

Figure 6:
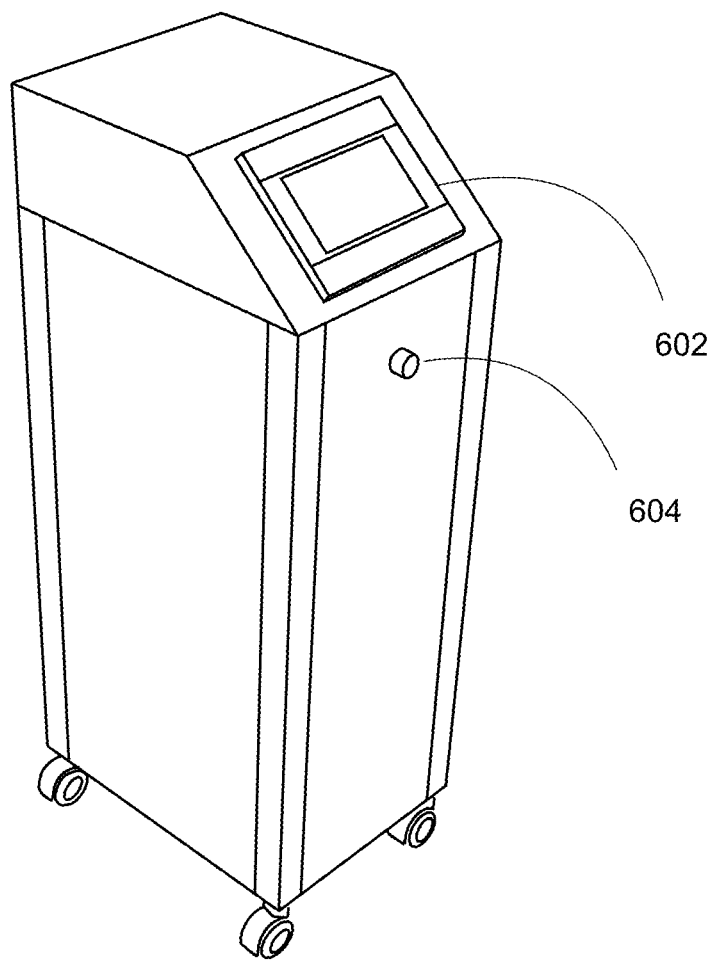
FIG. 6 is a perspective view of the system for generating and applying heated air to the human body in accordance with an embodiment of the invention.
Figure 7:
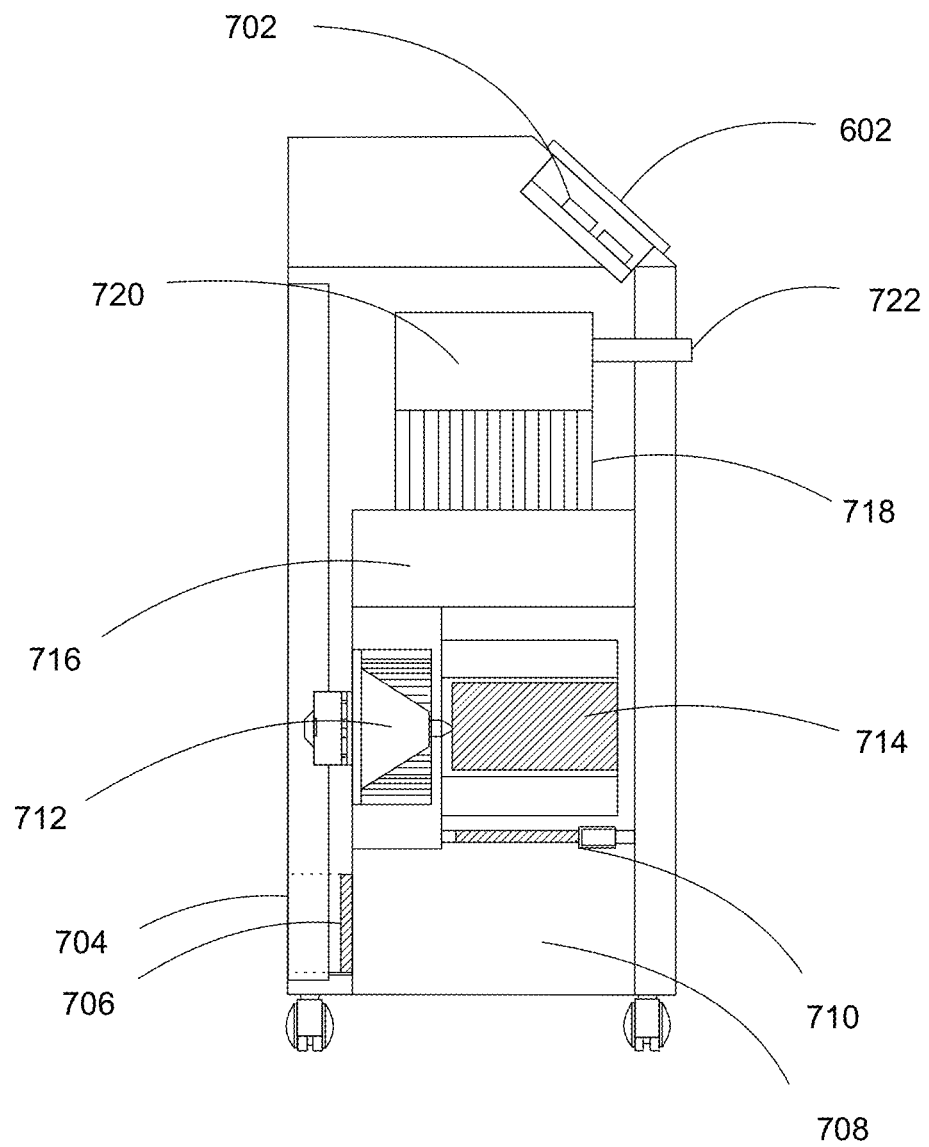
FIG. 7 is a cross sectional view of the system for generating and applying heated air to the human body in accordance with an embodiment of the invention.

FIG. 6 is a perspective view of the system for generating and applying heated air to the human body in accordance with an embodiment of the invention. In this view, the invention is a self contained, stand-up unit capable of being wheeled into patient rooms or around a patient's house. The invention includes a display 602 and an outlet hose FIG. 7 is a cross sectional view of the system for generating and applying heated air to the human body in accordance with an embodiment of the invention. The invention includes a display 602. A controller unit 702 can be implemented to govern every component of the system for generating and applying heated air to the human body. At its most basic, a controller could simply include a series of on-off switches to power each component. However, in the preferred embodiment, a controller unit may consist of at least one processor and memory including machine readable instructions which controls a plurality of basic electronic circuits which, in turn, governs each component. In embodiments of the invention, the controller unit 702 can be networked into a hospital's telemetry network, a home care patient monitoring network, or to any other suitable network. Persons having skill in the art will further appreciate that such a system and method can be implemented with other "smart" technologies such as utilities and telecommunication networks. An interface such as a touch screen display 602 such as an LCD display, a LCD touchscreen or dial or other functional equivalent can be configured to the controller unit 702. In larger healthcare settings, multiple systems may be employed and networked together. In other embodiments, the controller unit may be programmed manually or may operate on pre-installed software or firmware.

The controller unit 702 can include a display unit 602. The controller unit 702 may include a plurality of various selectors that enable a user to interact with the controller unit 702 and thereby enter input related to the operation of the system for producing and storing hot air, and for applying the stored hot air to a human body. By way of example, and not limitation, the controller unit 702 may include a power selector to turn the system on or off, a button temperature selector for choosing a desired temperature to be used when a user interacts with the controller unit 702, a programming selector for setting user-defined operation cycles, and a pump or blower speed selector for adjusting metrics such as pressure and flow rate. Other examples of selectors include a start/stop selector to initiate, pause, and/or resume an operation cycle and a stop selector or to terminate or pause an operation cycle. Persons having skill in the art will readily appreciate that numerous means of performing such functions are available.

In the preferred embodiment of the invention, a 110 volt power source is used. However, other power sources may be configured to operate the system depending on location and power availability. The components are 24 volt components known and appreciated in the art. The electric components can be governed through a controller unit 702. Persons having skill in the art will appreciate that numerous means and methods can be employed to implement such a system.

The invention further includes an air inlet 704 and an air chamber for receiving air 706. Embodiments of the invention include a filtering and sanitizing mechanism for filtering and sanitizing air entering the system for generating and applying heated air to the human body. The filtering and sanitizing mechanism can include, but is not limited to, a pre filter 706, a germicidal UV lamp 710 and a HEPA filter 714. Such a filtering and sanitizing mechanism can be used to filter particulate matter from the ambient air as well as apply germicidal UV radiation to incoming air as well. The result is filtered and sanitized air being applied to the human body.

The invention further includes an air blower for moving air from the air inlet through the hot air and storing apparatus 712. Persons having skill in the art will readily appreciate that numerous means of moving air from the air inlet through the hot air storing apparatus and to the human body can be used. In one embodiment, a traditional vacuum pump mechanism can be used. In another embodiment, a fan mechanism can be used. In yet another embodiment, an air compressor mechanism can be used.

The invention further includes a heating apparatus 718 configured to heat air to a desired temperature. The heating apparatus can include a temperature setting gauge configured to allow a user to set a desired temperature to heat the air, a pressure gauge to measure a pressure of the air, a pump to pump the hot air, and a fill connection.

The invention also includes a hot air chamber 720 for receiving the hot air from the heating apparatus and storing the hot air therein, the hot air chamber including a valve to connect to the fill connection of the heating apparatus such that the hot air chamber can receive the hot air from the heating apparatus. The invention can also include an insulated case for receiving the hot air chamber therein, the insulated case comprising a material having insulative properties to retain heat in the hot air chamber.

The invention further includes a flow release valve 722 which is configured to allow a user to adjust a flow amount of hot air being release by, for example, using a touchscreen display to adjust the flow release valve 722. The flow release valve may also include a manual valve including an off position, at which no air is released, and it may allow progressively more air to be release as the valve 722 is turned away from the off position. A connector 724 is adapted to connect the air holding portion of the container 720 to a flexible hose 726. The flow release valve may be positioned on either side of the connector 724, although in a preferred embodiment, the flow release valve is positioned between the connector 312 and the hot air chamber 720.

The flexible tube 726 allows for a nozzle 728 to be positioned by a user as desired to direct the hot air to from the hot air chamber to a desired location. The flexible tube 726 may be made from various flexible materials, such as rubber, plastic, polyurethane, PVC, Nomex, Hypalon, thermoplastic, etc.

Figure 8:
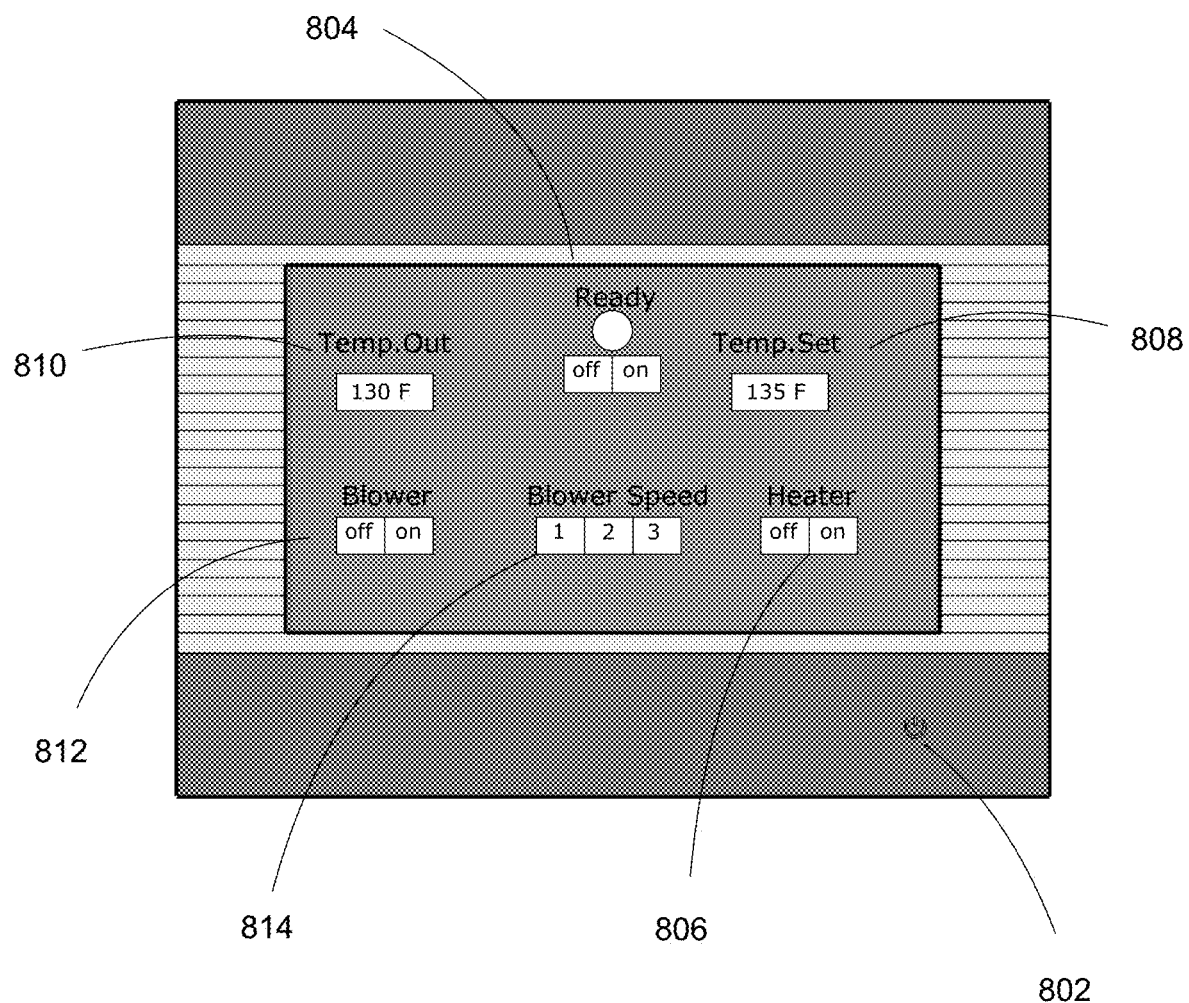
FIG. 8 is a front view of a display unit of a system for generating and applying heated air to the human body in accordance with an embodiment of the invention.

FIG. 8 is a front view of a display unit of a system for generating and applying heated air to the human body in accordance with an embodiment of the invention. A heater switch 806 allows a user to turn the heating apparatus on or off. The temperature of the hot air can be set using the temperature gauge 810, which can be set to read either Celsius or Fahrenheit. A temperature control 808 can be used to adjust the temperature to a desired level, such as with a numeric keypad or touchscreen, or even from a remote source connected to the system. In alternative embodiments, a pressure gauge can be used to monitor pressure in psi, for example. The system can be configured to pump hot air into a container to fill the container to a desired pressure. The system can be configured to automatically shut off the pumping of the hot air when the container reaches the desired or a preset pressure.

The system power on/off switch 802 can be used to turn on or off all power to the system. The power may be supplied through a convention power cord, or be supplied by one or more batteries within the system. The system may be configured to have one or more containers receive hot air at any desired temperature and until full. In preferred embodiments, the system may fill containers until a full pressure is reached, and the full pressure may be 20 psi as shown in FIG. 1, although other pressures could be used. The system may be configured to automatically stop pumping hot air when the full pressure is reached.

The ready light 804 can be used to indicate when the system is ready to begin pumping air at the desired temperature. The system may need time to warm up a heating element to produce hot air of the desired temperature, and the ready light can thus be used to indicate when the apparatus is sufficiently warmed up to begin pumping the heated air. connector of a particular type.

The blower on/off switch 812 is used to turn the blower (or pump) on (or off) to begin (or stop) pumping hot air into the container for receiving hot air. In some embodiments, the switch may be configured to not function until the ready light is lit indicating the air can be pumped at the desired temperature. In one embodiment, the blower or pump speed can be adjusted through a touch screen mechanism 814.

Figure 9:
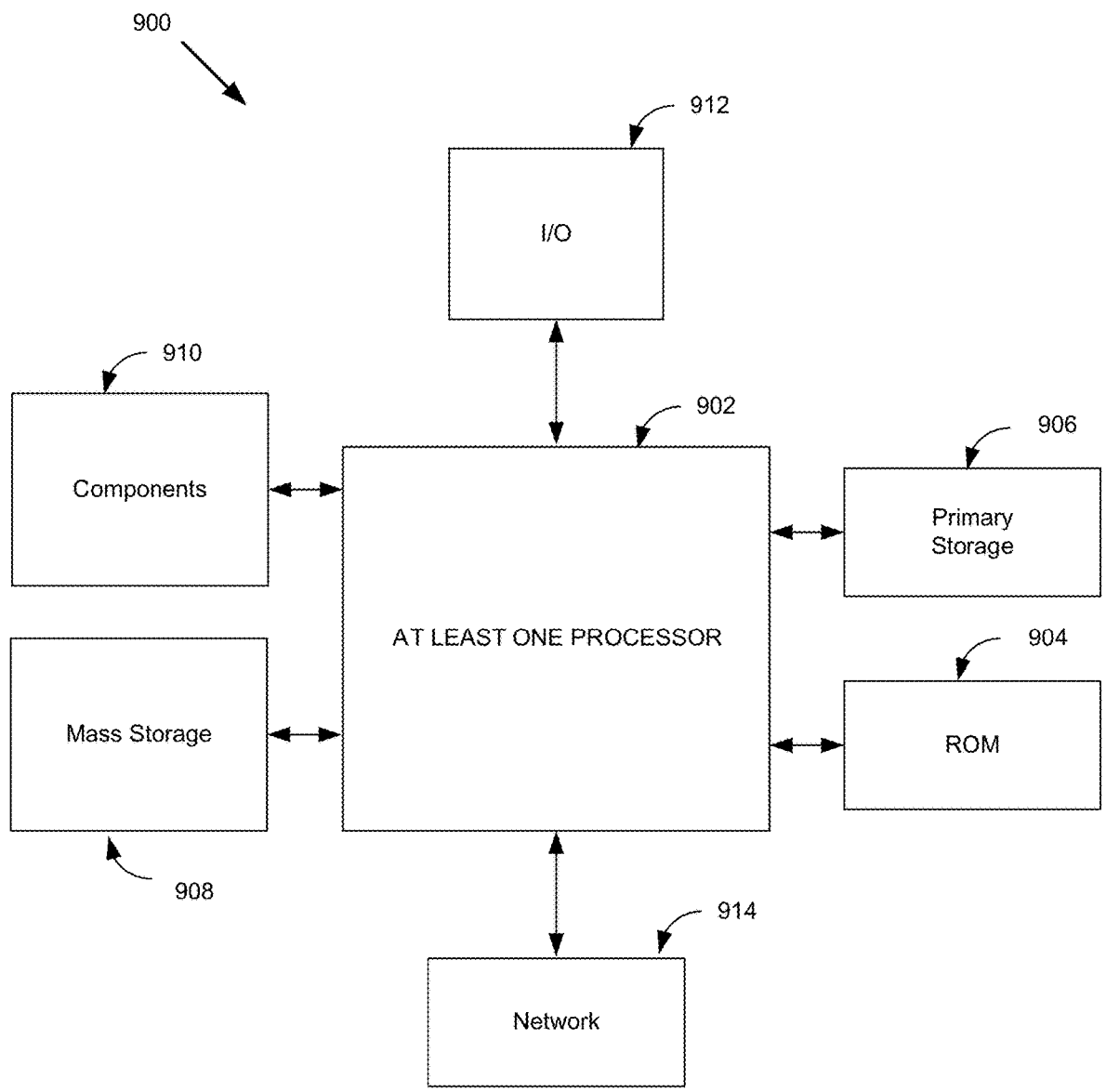
FIG. 9 is a block diagram of a typical computer system that, when appropriately configured or designed, may serve as a computer system for which the controller unit of the system for generating and applying heated air to the human body, and the components thereof, may be embodied.

FIG. 9 is a block diagram of a typical computer system that, when appropriately configured or designed, may serve as a computer system or controller unit of the system for generating and applying heated air to the human body, and the components thereof, may be embodied. The computer system 900 includes at least one processor 902 (also referred to as central processing units, or CPUs) that may be coupled to storage devices including a primary storage 906 (typically a random-access memory, or RAM), a primary storage 904 (typically a read-only memory, or ROM). CPU 902 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors. As is well known in the art, primary storage 904 acts to transfer data and instructions uni-directionally or bi-directionally to the CPU and primary storage 906 typically may be used to transfer data and instructions in a bi-directional manner. The primary storage devices discussed previously may include any suitable computer-readable media known and appreciated in the art. A mass storage device 908 may also be coupled bi-directionally to CPU 902 and provides additional data storage capacity and may include any of the computer-readable media described above. Mass storage device 908 may be used to store programs, data and the like and typically may be used as a secondary storage medium such as a hard disk. It will be appreciated that the information retained within mass storage device 908, may, in appropriate cases, be incorporated in standard fashion as part of primary storage 906 as virtual memory.

The CPU is coupled to the various components 910 of the invention such as the sensor array, the solenoid valves, the heating unit, the drive motor and drive gear assembly, the switches and buttons. The CPU 902 may also be coupled to an interface 912 that connects to one or more input/output devices such as buttons, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 902 optionally may be coupled to an external device such as a database or a computer or telecommunications or internet network using an external connection shown generally as a network 914, which may be implemented as a hardwired or wireless communications link using suitable conventional technologies. With such a connection, the CPU might receive information from the network, or might output information to the network in the course of performing the method steps described in the teachings of the present invention.

It will be understood by persons having skill in the art that memory storing computer readable instructions that, when executed by the at least one processor, cause the system for generating and applying heated air to the human body, by at least one processor, to perform the steps of powering up and starting the system, powering up a heating apparatus configured to heat air to a desired temperature, setting the temperature of the air stored in the container for receiving hot air from the heating apparatus, engaging the air blower, adjusting the flow release mechanism connected to an outlet of the container for receiving hot air from the heating apparatus, and powering down the system.

It will be further understood by persons having skill in the art that memory storing computer readable instructions that, when executed by the at least one processor, cause the system for generating and applying heated air to the human body, by at least one processor, to perform the steps of powering up and starting the system, powering up a heating apparatus configured to heat air to a desired temperature, adjusting the temperature of the air stored in the container for receiving hot air from the heating apparatus, engaging the air blower, engaging the UV sanitizer, adjusting the flow release mechanism connected to an outlet of the container for receiving hot air from the heating apparatus, and powering down the system.

Figure 10:
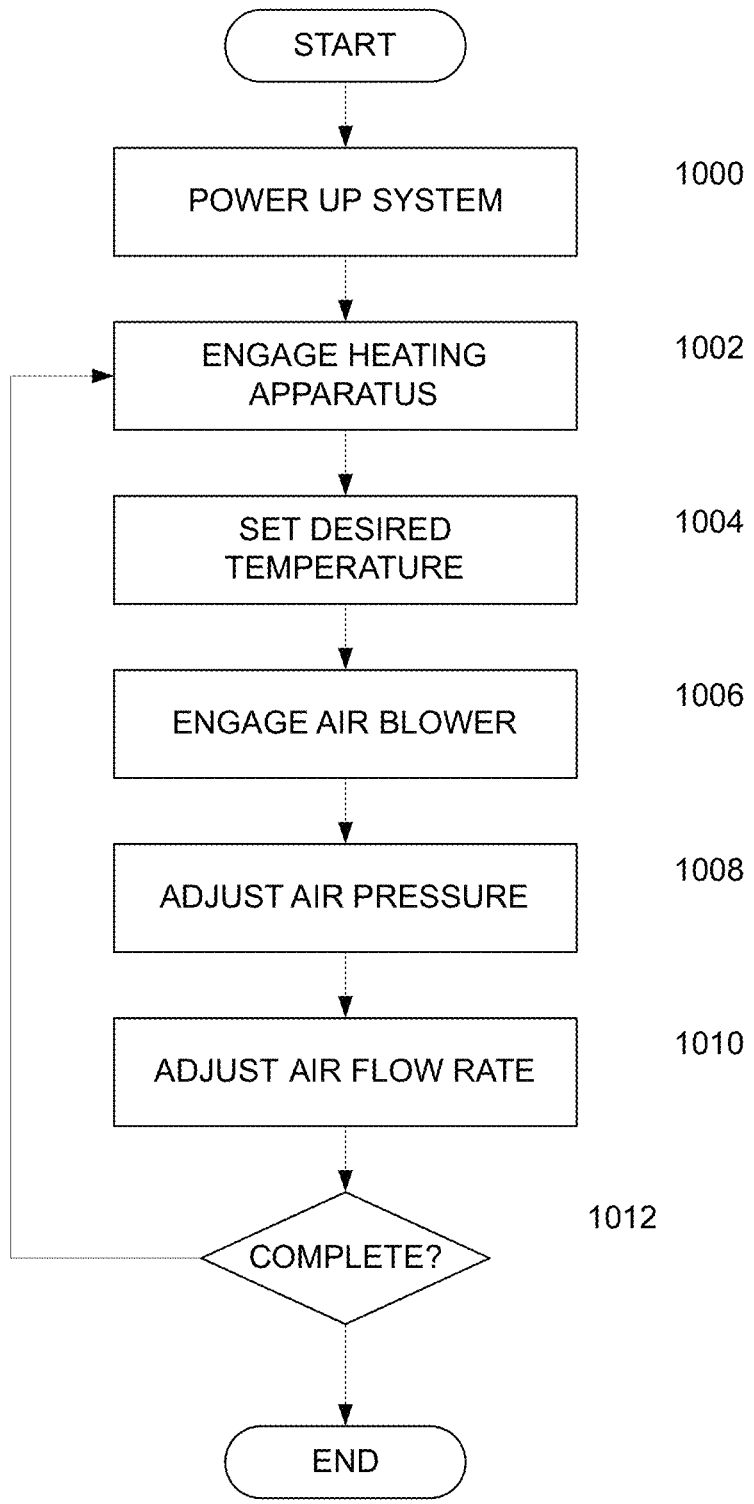
FIG. 10 is a flow diagram of a method for generating and applying heated air to the human body using a system for generating and applying heated air to the human body in accordance with an embodiment of the invention.

FIG. 10 is a flow diagram of a method for generating and applying heated air to the human body using a system for generating and applying heated air to the human body in accordance with an embodiment of the invention. The steps of such a flow diagram may be readily implemented through the use of a networked or non-networked controller unit 702 using a microprocessor or microcontroller means. A user can program metrics of the system's timing cycle through the controller unit. Such metrics include, but are not limited to, powering up the system 1000, powering up a heating apparatus configured to heat air to a desired temperature 1002, setting the temperature of the air stored in the container for receiving hot air from the heating apparatus 1004, engaging the air blower 1006 adjusting the flow release mechanism connected to an outlet of the container for receiving hot air from the heating apparatus, adjusting the air pressure in the container for receiving hot air from the heating apparatus 1008, adjusting the air flow rate for the air emerging from the system 1010, and powering down the system when the heating cycle is complete.

The system is first powered up and the system for producing and storing hot air, and for applying the stored hot air to a human body starts 1000. For example, and not by way of limitation, the unit may be powered up by pressing a button on a touch screen display. In other embodiments of the invention, the system can be manually started by pressing a button or switch on the controller unit 702.

The system will then prompt a user to engage the heating apparatus 1002. When activated, the controller unit will engage the heating apparatus configured to heat air to a temperature. In other embodiments of the invention, the heating apparatus can be engaged manually through means such as, but not limited to, toggle switches or buttons.

The system will then prompt a user to set the desired temperature of the air to be applied to a human body 1004. In the preferred embodiment of the invention, the controller unit will provide reasonable parameters governing the temperature of the air. By way of example, air exceeding 150 degrees will automatically shut down the system for safety purposes.

The system will then prompt a users to engage the air pump or air blower 1006. By engaging the air pump or air blower, air will be drawing into the system through an air inlet and drawing through a heating apparatus where air is heated to a desired temperature and is stored in a container or air chamber.

The system will then allow a user to adjust the air pressure in various parts of the system 1008. By way of example, but not limitation, sensors in the air inlet or heated air container. Persons having skill in the art will appreciate that air pressure can be adjusted through numerous means involving an air pump or air blower and air inlets and outlets.

The system will further allow a user to adjust the air flow rate of heated air emerging from the system to be applied to a human body 1010. By way of example, and not limitation, the air flow rate can be adjusted by adjusting the speed of the air pump or air blower.

The system will allow a user to determine when the cycle is complete 1012. In some embodiments of the invention, if no use is detected after a certain amount of time, the system will automatically shut down.

Further instructions may include the use of a germicidal UV sanitizer to provide sanitary heated air. Additional instructions can include timers, automation and variations of the aforementioned features.

Having fully described at least one embodiment of the system for generating and applying heated air to the human body, other equivalent or alternative methods of implementing such a system for generating and applying heated air to the human body according to the present invention will be apparent to those skilled in the art. Various aspects of the invention have been described above by way of illustration, and the specific embodiments disclosed are not intended to limit the invention to the particular forms disclosed. The particular implementation of the system for generating and applying heated air to the human body may vary depending upon the particular context or application. By way of example, and not limitation, the system and method for the system for generating and applying heated air to the human body described in the foregoing was principally directed to provide heated air to the human body in a managed care setting. However, similar techniques may instead be applied to other instances where such a device is required, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Although specific features of the system for generating and applying heated air to the human body are shown in some drawings and not others, persons skilled in the art will understand that this is for convenience. Each feature may be combined with any or all of the other features in accordance with the invention. The words "including," "comprising," "having," and "with" as used herein are to be interpreted broadly and comprehensively, and are not limited to any physical interconnection. Claim elements and flowchart steps herein may have been numbered and/or lettered solely as an aid in readability and understanding. Any such numbering and lettering in itself is not intended to and should not be taken to indicate the ordering of elements and/or steps in the claims to be added at a later date.

Any amendment presented during the prosecution of the application for this patent is not a disclaimer of any claim element presented in the description or claims to be filed. Persons skilled in the art cannot reasonably be expected to draft a claim that would literally encompass each and every equivalent.

What is claimed is:

1. A system for producing and storing hot air, and for applying the stored hot air to a human body, comprising:
    a. a heating apparatus configured to heat air to a desired temperature, the heating apparatus including a temperature setting gauge configured to allow a user to set a desired temperature to heat the air,
    b. a pressure gauge to measure a pressure of the air,
    c. a pump to pump the hot air,
    d. a fill connection;
    e. a container for receiving hot air from the heating apparatus and storing the hot air therein, the container consisting of a rigid material and including at least one valve to connect to the fill connection of the heating apparatus such that the container can receive the hot air from the heating apparatus
    f. an adjustable flow release mechanism connected to an outlet of the container for receiving the hot air, the adjustable flow release mechanism being configured to allow a user to adjust an amount of flow of hot air out of the said container; and
    g. a flexible hose connected to the adjustable flow release mechanism, the flexible hose having a nozzle configured to direct the hot air out of the flexible hose, wherein the flexible hose allows a user to direct the hot air to a portion of the human body.

2. The system of claim 1, further comprising an insulated case for receiving the container for receiving hot air therein, the insulated case comprising a material having insulative properties to retain heat in the hot air in the container for receiving the hot air.

3. The system of claim 2, wherein the insulated case comprises a material having insulative and expandable properties.

4. The system of claim 2, wherein the insulated case comprises a material selected from a quilted material, Thinsulate®, or other thermal fabric material.

5. The system of claim 2, further comprising attachment points on the insulated case for attaching the hot air producing system to an object.

6. The system of claim 1, wherein the pump is configured to automatically stop pumping the hot air when the pressure gauge reaches a full pressure.

7. A system for producing and storing hot air, and for applying the stored hot air to a human body, comprising:
    a. a heating apparatus configured to heat air to a desired temperature, the heating apparatus including a temperature setting gauge configured to allow a user to set a desired temperature to heat the air,
    b. a pressure gauge to measure a pressure of the air,
    c. a heating apparatus configured to heat air to a desired temperature,
    d. an air blower for moving air from an air inlet through the system for producing and storing hot air, and for applying the stored hot air to a human body;
    e. a fill connection;
    f. a hot air chamber for receiving hot air from the heating apparatus and storing the hot air therein, the container including at least one valve to connect to the fill connection of the heating apparatus such that the hot air chamber can receive the hot air from the heating apparatus;

g. an adjustable flow release mechanism connected to an outlet of the hot air chamber for receiving the hot air, the adjustable flow release mechanism being configured to allow a user to adjust an amount of flow of hot air out of the said hot air chamber;

h. a flexible hose connected to the adjustable flow release mechanism, the flexible hose having a nozzle configured to direct the hot air out of the flexible hose, wherein the flexible hose allows a user to direct the hot air to a portion of the human body;

i. a controller unit including at least one processor; and j. a display.

8. The hot air producing and storing apparatus of claim 7, further comprising an adjustable flow release mechanism connected to an outlet of the hot air chamber, the adjustable flow release mechanism being configured to allow a user to adjust an amount of flow of hot air out of the hot air chamber.

9. The system of claim 7 further comprising memory storing computer readable instructions, when executed by the controller unit including at least one processor, enable a user to:
  a. power up the system;
  b. engage the heating apparatus configured to heat air to a desired temperature;
  c. set the desired temperature of air to be heated and stored;
  d. engage the air blower;
  e. adjust the air pressure in the container for receiving hot air; and
  f. adjust the flow rate of air emerging from the system.

10. The system of claim 9 wherein the display is a touch screen display.

11. The hot air producing and storing apparatus of claim 9, wherein the container for receiving heated air is surrounded by an insulative material.

12. The system of claim 7, wherein the container for receiving heated air comprises a material having elastic properties.

13. The system of claim 7, wherein the container comprises a material having rigid properties.

14. The system of claim 7, wherein the pump is configured to automatically stop pumping the hot air when the pressure gauge reaches a full pressure.

15. The system of claim 7, further comprising attachment points on the insulated case for attaching the hot air producing and storing apparatus to an object.

16. A system for producing and storing hot air, and for applying the stored hot air to a human body, comprising:
  a. an air inlet;
  b. an air chamber for receiving air;
  c. a filtering and sanitizing mechanism for filtering and sanitizing air entering the system for producing and storing hot air;
  d. an air blower for moving air from the air inlet the air chamber for receiving air;
  e. a heating apparatus configured to heat air to a temperature, the heating apparatus including a temperature setting gauge configured to allow a user to set a desired temperature to heat the air, a pressure gauge to measure a pressure of the air, a pump to pump the hot air, and a fill connection;
  f. a hot air chamber for receiving the hot air from the heating apparatus and storing the hot air therein, the hot air chamber including a valve to connect to the fill connection of the heating apparatus such that the hot air chamber can receive the hot air from the heating apparatus;
  g. an insulated case for receiving the hot air chamber therein, the insulated case comprising a material having insulative properties to retain heat in the hot air chamber;
  h. a flexible hose connected to the adjustable flow release mechanism, the flexible hose having a nozzle configured to direct the hot air out of the flexible hose, wherein the flexible hose allows a user to direct the hot air to a portion of the human body;
  i. a controller unit including at least one processor; and
  j. a display.

17. The hot air producing and storing apparatus of claim 16, further comprising an adjustable flow release mechanism connected to an outlet of the hot air chamber, the adjustable flow release mechanism being configured to allow a user to adjust an amount of flow of hot air out of the hot air chamber.

18. The system of claim 16 further comprising memory storing computer readable instructions, when executed by the controller unit including at least one processor, enable a user to:
  a. power up the system;
  b. engage the heating apparatus configured to heat air to a desired temperature;
  c. set the desired temperature of air to be heated and stored;
  d. engage the air blower;
  e. engage the UV sanitizer;
  f. adjust the air pressure in the container for receiving hot air; and
  g. adjust the flow rate of air emerging from the system.

19. The system of claim 5 wherein the display is a touch screen display.

* * * * *